(12) United States Patent
Okamoto (10) Patent No.: US 6,919,210 B1
(45) Date of Patent: Jul. 19, 2005

(54) METHOD FOR IDENTIFYING AUTOIMMUNE DISEASE, METHOD FOR DETECTING ANTI-REG PROTEIN AUTOANTIBODY AND DIAGNOSTICS FOR AUTOIMMUNE DISEASE

(75) Inventor: Hiroshi Okamoto, 15-3-205, Tsunogoro 2-chome, Aoba-ku, Sendai-shi, Miyagi 980-0874 (JP)

(73) Assignee: Hiroshi Okamoto, Miyagi (JP)

( * ) Notice: Subject to any disclaimer, the term of this patent is extended or adjusted under 35 U.S.C. 154(b) by 0 days.

(21) Appl. No.: 09/958,447

(22) PCT Filed: Apr. 6, 2000

(86) PCT No.: PCT/JP00/02245

§ 371 (c)(1),
(2), (4) Date: Oct. 5, 2001

(87) PCT Pub. No.: WO00/62066

PCT Pub. Date: Oct. 19, 2000

(30) Foreign Application Priority Data

Apr. 7, 1999 (JP) .......................................... 11-099963

(51) Int. Cl.[7] ..................... C07K 14/475; G01N 33/546; G01N 33/564
(52) U.S. Cl. ......................... 436/506; 435/7.1; 435/7.9; 435/69.3; 435/69.4; 435/975; 436/503; 436/524; 436/528; 436/534; 436/536; 436/811; 530/396; 530/403; 530/806; 530/845
(58) Field of Search ................. 436/503, 506, 436/524, 528, 536, 811, 534; 435/7.8, 7.9, 69.3, 69.4, 975, 7.95, 7.1; 530/396, 403, 806, 845

(56) References Cited

U.S. PATENT DOCUMENTS 5,837,841 A 11/1998 Bandman et al.
5,866,546 A 2/1999 Gross et al. .................. 514/21

FOREIGN PATENT DOCUMENTS

| EP | 0 286 114 | 10/1988 |
|---|---|---|
| EP | 0 303 233 | 2/1989 |
| EP | 0 369 797 A2 | 6/1990 |
| JP | 01132388 | 5/1989 |
| JP | 1-137994 | 5/1989 |

OTHER PUBLICATIONS

Kimio Terazono, et al., "A Novel Gene Activated in Regenerating Islets," The Journal of Biological Chemistry, vol. 283, No. 5, pp. 2111–2114 1988.

Jacqueline Carrère, et al., "Human pancreatic reg protein Immunoenzymatic assay and molecular form in serum," Clinica Chimica Acta, vol. 273, pp. 185–194, 1998.

David J. Gross, et al., "Amelioration of Diabetes in Nonobese Diabetic Mice with Advanced Disease by Linomide–Induced Immunoregulation Combined with Reg Protein Treatment," Endocrinology, vol. 139, No. 5, pp. 2369–2374, 1998.

C. Ishi, et al. "Appearance of a Regenerating (Reg) Gene Protein in Pancreatic Islets of Remission BB/WOR/TKY Rats", Endocrine Journal, vol. 40, No. 1993, pp. 269–273.

Y.Yonemura, "Sui Ra Tou Saisai to reg Idenshi", Saibou Kougaku, vol. 13, No. 9, 1994, pp. 776–783 (with a partial translation), Translation Only Considered.

H. Okamoto, "Autoantibody Against Reg I Protein in Nidm Patients", Diabetes, vol. 48 (Supplement1), 1999, p. A444.

H. Okamoto, "Igaku no Ayumi, Bessatsu, Jun.", 1999, pp. 153–157 (with a partial translation), Translation Only Considered.

Itoh, "Isolation and Characterization of Human reg Protein Produced in *Saccharomyces cerevisiae*," FEBS Letters, vol. 272, No. 1,2, pp. 85–88, Oct. 1990.

Supplementary European Search Report completed on Nov. 10, 2004, and issued to a related foreign application.

*Primary Examiner*—Christopher L. Chin
*Assistant Examiner*—James L. Grun
(74) *Attorney, Agent, or Firm*—Knobbe, Martens, Olson & Bear, LLP (57) ABSTRACT

A method for judging an autoimmune disease by detecting the existence of an anti-Reg protein autoantibody in a specimen; and a method for judging insulin-dependent or non-insulin-dependent diabetes mellitus.

A method for detecting an anti-Reg protein autoantibody by bringing into a specimen into contact with an antigen component and detecting the formation of an immune complex.

A reagent for diagnosing autoimmune disease which contain an antigen component capable of binding specifically to the anti-Reg protein autoantibody; and a reagent for diagnosing insulin-dependent or non-insulin-dependent diabetes mellitus.

11 Claims, 2 Drawing Sheets

METHOD FOR IDENTIFYING AUTOIMMUNE DISEASE, METHOD FOR DETECTING ANTI-REG PROTEIN AUTOANTIBODY AND DIAGNOSTICS FOR AUTOIMMUNE DISEASE

TECHNICAL FIELD

This application is the U.S. National Phase under 35 U.S.C. §371 of International Application PCT/JP00/02245, filed Apr. 6, 2000, which claims priority to Japanese Patent Application No. 11-99963, filed Apr. 7, 1999. The International Application was not published under PCT Article 21(2) in English.

The present invention relates to a method for identifying autoimmune diseases and diabetes mellitus (including insulin-dependent diabetes mellitus, non-insulin-dependent diabetes mellitus, etc.). The present invention also relates to a method for detecting an anti-Reg protein autoantibody, and a reagent diagnosing for autoimmune diseases and diabetes mellitus (including insulin-dependent diabetes mellitus, non-insulin-dependent diabetes mellitus, etc.).

BACKGROUND ART

Autoimmune diseases are diseases caused by an abnormal immune system in which the immune system does not work normally to produce humoral or cellular immune response to self-cells or self-tissues and an autoantibody responding to self-cells and self-tissues appear.

It is known that an autoantibody attacks self-cells or self-tissues to injure their function and as a result causes autoimmune diseases. Moreover, it has recently been reported that the autoantibody is detected in the patient's serum prior to occurrence of an autoimmune disease.

This means that detection of an autoantibody permits an early discovery or precognition of occurrence of an autoimmune disease, or precognition of deterioration of the disease condition, which allows early treatment or preventive therapy of the autoimmune disease.

Based on these findings, a variety of autoantibodies against autoantigens have been discovered and the autoantibodies against autoantigens have been measured in clinical tests.

For example, in a case of autoimmune diabetes mellitus, as relevant autoantibodies, an islet cell antibody (hereinafter abbreviated to ICA), islet cell surface antibody (hereinafter abbreviated to ICSA), anti-insulin antibody, anti-glutamic acid decarboxylase antibody, anti-ganglioside antibody, anti-bovine lactoalbumin antibody, anti-pancreatic cytokeratin antibody, and the like have been reported. In the above-mentioned autoimmune diabetes mellitus, ICA and ICSA can be detected in serum of the patients at a high frequency at the time of development of insulin-dependent diabetes mellitus (hereinafter abbreviated to IDDM). Particularly, ICA can be detected in serum of the patients prior to development of IDDM, which is accordingly known as a marker for preconceiving development of IDDM.

As mentioned above, many of IDDM patients are considered due to autoimmune diabetes mellitus developed in the autoimmune system, though it is reported that in some patients no autoantibody can be detected.

To the contrary, as for non-insulin-dependent diabetes mellitus (hereinafter abbrebiated to NIDDM), for example, the existence rate of ICA in IDDM patients is 40% or more, while that in NIDDM patients is deemed less than about 3% (Kobayashi T et al., Diabetes, Vol. 35, 335–340 (1986)). Thus, though the positive rate of autoantibody is high in IDDM, it is low in NIDDM, and there is no report on an effective autoantibody as a diagnostic marker for NIDDM.

On the other hand, a Reg (regeneration gene) protein was a protein discovered from the gene in which the expression is recognized markedly during regeneration of the Langerhans islets by administering nicotinamide to about 90% excised pancreas in rats (Terazono et al., Journal of Biological Chemistry, 263: 2111–2114 (1988)).

Reg proteins are found in human, rat, mouse, cattle, and hamster and now classified into three sub-types, i.e., Reg I, Reg II and Reg III, from the homology of their primary structures and the presence of the insertion sequence of 7 or 5 amino acid residues.

Reg proteins can be found not only in the above-mentioned Langerhans islet cells but also in liver, intestine, cancer cells in pancreas, and the mucous membrane of the small intestine, and reportedly appear during regeneration of nerve or gastric wall or at the time of development of pancreatitis. Accordingly, Reg proteins are considered widely involved in regeneration and proliferation of intracorporeal organs.

However, so far there is no report on the existence of autoantibodies against Reg proteins and autoimmune diseases caused thereby.

DESCRIPTION OF THE INVENTION

One of the objects of the present invention is to provide a method for identifying an autoimmune disease. Particularly, it is to provide a method for identifying diabetes mellitus, more particularly, a method for identifying insulin-dependent diabetes mellitus and non-insulin-dependent diabetes mellitus.

Another object of the present invention is to provide a method for detecting an antibody that can be used in diagnosis of autoimmune diseases.

Yet another object of the present invention is to provide a reagent for diagnosing autoimmune diseases. Particularly, it is to provide a reagent for diagnosing diabetes mellitus, more particularly, a reagent for diagnosing insulin-dependent diabetes mellitus and non-insulin-dependent diabetes mellitus.

The present invention relates to the following items (1)–(24).

(1) A method for identifying an autoimmune disease, which comprises the step of detecting the existence of an anti-Reg protein autoantibody in a specimen.

(2) A method for identifying diabetes mellitus, which comprises the step of detecting the existence of an anti-Reg protein autoantibody in a specimen.

(3) A method for identifying insulin-dependent diabetes mellitus, which comprises the step of detecting the existence of an anti-Reg protein autoantibody in a specimen.

(4) A method for identifying non-insulin-dependent diabetes mellitus, which comprises the step of detecting the existence of an anti-Reg protein autoantibody in a specimen.

(5) A method for detecting an anti-Reg protein autoantibody, which comprises the steps of bringing a specimen into contact with an antigen component capable of binding specifically to the anti-Reg protein autoantibody and detecting the formation of an immune complex resulting from the reaction of the anti-Reg protein autoantibody with the antigen component capable of binding specifically to the anti-Reg protein autoantibody.

(6) A method for detecting an anti-Reg protein autoantibody according to (5), wherein the antigen component capable of binding specifically to the anti-Reg protein autoantibody is a Reg protein.

(7) A method for detecting an anti-Reg protein autoantibody according to (5), wherein the antigen component capable of binding specifically to the anti-Reg protein autoantibody is a part of Reg protein.

(8) A method for detecting an anti-Reg protein autoantibody according to (6) or (7), wherein the antigen component capable of binding specifically to the anti-Reg protein autoantibody is an artificially synthesized Reg protein.

(9) A reagent for diagnosing an autoimmune disease, which comprises an antigen component capable of binding specifically to the anti-Reg protein autoantibody.

(10) A reagent for diagnosing an autoimmune disease according to (9), wherein the antigen component capable of binding specifically to the anti-Reg protein autoantibody is a Reg protein.

(11) A reagent for diagnosing an autoimmune disease according to (9), wherein the antigen component capable of binding specifically to the anti-Reg protein autoantibody is a part of Reg protein.

(12) A reagent for diagnosing an autoimmune disease according to (10) or (11), wherein the antigen component capable of binding specifically to the anti-Reg protein autoantibody is an artificially synthesized Reg protein.

(13) A reagent for diagnosing diabetes mellitus, which comprises an antigen component capable of binding specifically to the anti-Reg protein autoantibody.

(14) A reagent for diagnosing diabetes mellitus according to (13), wherein the antigen component capable of binding specifically to the anti-Reg protein autoantibody is a Reg protein.

(15) A reagent for diagnosing diabetes mellitus according to (13), wherein the antigen component capable of binding specifically to the anti-Reg protein autoantibody is a part of Reg protein.

(16) A reagent for diagnosing diabetes mellitus according to (14) or (15), wherein the antigen component capable of binding specifically to the anti-Reg protein autoantibody is an artificially synthesized Reg protein.

(17) A reagent for diagnosing insulin-dependent i) diabetes mellitus, which comprises an antigen component capable of binding specifically to the anti-Reg protein autoantibody.

(18) A reagent for diagnosing insulin-dependent diabetes mellitus according to (17), wherein the antigen component capable of binding specifically to the anti-Reg protein autoantibody is a Reg protein.

(19) A reagent for diagnosing insulin-dependent diabetes mellitus according to (17), wherein the antigen component capable of binding specifically to the anti-Reg protein autoantibody is a part of Reg protein.

(20) A reagent for diagnosing insulin-dependent diabetes mellitus according to (18) or (19), wherein the antigen component capable of binding specifically to the anti-Reg protein autoantibody is an artificially synthesized Reg protein.

(21) A reagent for diagnosing non-insulin-dependent diabetes mellitus, which comprises an antigen component capable of binding specifically to the anti-Reg protein autoantibody.

(22) A reagent for diagnosing non-insulin-dependent diabetes mellitus according to (21), wherein the antigen component capable of binding specifically to the anti-Reg protein autoantibody is a Reg protein.

(23) A reagent for diagnosing non-insulin-dependent diabetes mellitus according to (21), wherein the antigen component capable of binding specifically to the anti-Reg protein autoantibody is a part of Reg protein.

(24) A reagent for diagnosing non-insulin-dependent diabetes mellitus according to (22) or (23), wherein the antigen component capable of binding specifically to the anti-Reg protein autoantibody is an artificially synthesized Reg protein.

The method for identifying autoimmune diseases in the present invention aims to diagnose or to predict autoimmune diseases caused by an anti-Reg protein autoantibody by detecting the existence of the anti-Reg protein autoantibody in a specimen.

The autoimmune diseases which can be diagnosed or predicted by detection of the existence of the anti-Reg protein autoantibody, which is not particularly limited as long as they are caused by the existence of the anti-Reg protein autoantibody, include, for example, diabetes mellitus, insulin-dependent diabetes mellitus, non-insulin-dependent diabetes mellitus, hepatoma, colon cancer, cancer of small intestine, pancreatitis, gastric ulcer, and Alzheimer's disease. Among them, diabetes mellitus is preferred in view of high positive rate, and more preferred are insulin-dependent diabetes mellitus and non-insulin-dependent diabetes mellitus.

In the present invention, the anti-Reg protein autoantibodies to be detected, which are not particularly limited as long as they react with Reg proteins, include, for example, the classes of IgG antibody, IgM antibody, IgA antibody, IgD antibody and IgE antibody, reacting with Reg proteins. Among the above classes of antibodies reacting with Reg proteins, it is preferred to detect an IgG antibody or an IgM antibody since they are found abundantly in patients suffering from autoimmune diseases.

In the present invention, as the anti-Reg protein antibody used in detection, any from the above classes of antibody may be detected alone or in a combination of two or more.

The specimens to be used in the present invention, which are not particularly limited as long as they possibly contain the anti-Reg protein autoantibody, include, for example, body fluid such as blood, serum, plasma, urine and cerebrospinal fluid, and tissues such as Langerhans islet cells, pancreas, exocrine pancreatic glands, nerve cells and various cancer cells. Among them, blood, serum, plasma and urine are preferred because the specimens are easily available.

The antigen components used in the method for detecting an anti-Reg protein autoantibody of the present invention, which are not particularly limited as long as they can bind specifically to the anti-Reg protein autoantibody, preferably include Reg proteins in view of their specificity. More particularly, a part of a Reg protein is preferred. Moreover, Reg proteins that are artificially produced by genetic recombination or chemical syntheses are preferred since they can be obtained in a stable form in quantity.

As for Reg proteins, there is no limitation as long as a genetic product of Reg protein from a gene reported as a Reg gene family is used (Umino et al., Nippon Rinsho, Vol. 55, p.817–821; Yonekura H, et al., In: Flatt PR et al. (eds) Frontiers of Insulin Secretion and Pancreatic B-Cell Research, Smith-Golden, London, pp 581–588; Miyashita H et al., FEBS Letter Vol. 377, p. 429–433 (1995)). For example, human Reg protein Iα, Reg Iβ, HIP (a gene expressed in hepatocellular carcinoma, intestine, pancreas), PAP (the gene for pancreatitis associated protein), RS (Reg-related sequence), rat's Reg I, PAP I, II, III, murine Reg I, II, IIIα, IIIβ, IIIγ, IIIδ, hamster's INGAP (islet neogenesis associated protein), bovine PTP (pancreatic thread protein), and the like are included.

As for the human Reg proteins, Terazono et al. (Journal of Biological Chemistry, Vol. 263, 2111–2114 (1988)), Moriizumi S et al. (Biochimica et Biophysica Acta, Vol. 1217, 199–202 (1994)), Lasserre C et al. (Cancer Research, Vol. 52,5089–5095 (1992)) and Lasserre C et al. (European Journal of Biochemistry, Vol. 224, 29–38 (1994)) describe their sequences and the like in detail.

The above-mentioned Reg proteins can be appropriately selected according to a type of autoimmune diseases to be detected. In view of the specificity of detection of the anti-Reg protein autoantibody, Reg proteins existing in the organs injured are preferred. For example, when the disease to be diagnosed is diabetes mellitus, insulin-dependent diabetes mellitus or non-insulin-dependent diabetes mellitus, human Reg Iα protein is preferred.

As for the antigen components used in the method for detection of an anti-Reg protein autoantibody of the present invention, it is possible to use the fragmentated Reg proteins by means of well-known enzymatic procedures or genetic recombination technique or the partially modified Reg proteins by means of well-known enzymatic procedures or genetic recombination technique, in view of their sensitivity and specificity in detection of the anti-Reg protein autoantibody as well as the stability of antigenic activity during preservation as a diagnostic reagent for a long period.

In the present invention, as the anti-Reg protein used in detection of the anti-Reg protein autoantibody, any of the above Reg proteins may be used alone or in a combination of two or more.

As a method for producing the above-mentioned Reg proteins of the present invention, though there is no particular limitation, an artificial method such as genetic recombination or chemical synthesis, or purification from organs, body fluid or secrete may be adapted.

In the method for producing Reg proteins by means of genetic recombination, for example, a DNA coding for the above Reg protein is inserted into a vector to produce a recombinant vector. This is then transformed into a host to form a transformant, which is then incubated to utilize the transformant per se or the supernatant of the culture.

DNA coding for a Reg protein, which is inserted into a recombinant vector, may be DNA coding for the full length of the above Reg protein or a part thereof.

The recombinant vector may be prepared by inserting a DNA coding for the above Reg protein into a plasmid vector or phage vector that can be replicated in a host cell in a conventional manner. In this operation, if necessary, a linker may be used.

As the plasmid vectors, those containing a drug resistant gene such as kanamycin-resistant gene, ampicillin-resistant gene, etc., may preferably be used because such vectors permit easy screening of a transformant containing the recombinant vector to be made and maintain the recombinant vector stably in a host cell.

Specific examples of plasmid vectors include plasmids pPIC3.5K, pPIC9K, pAO815, pYX011, pYX111, pUC118, pUB110, and the like. pPIC3.5K, pPIC9K, and pAO815 can be purchased from Funakoshi Co., Ltd., pYX011 and pYX111 from Cosmo Bio Co., Ltd., and pUC118 and pUB110 from Takara Shuzo Co., Ltd., respectively.

Specific examples of phage vectors include λgt11 phage, λgt10 phage, and the like. The λgt11 phage and λgt10 phage can be purchased from Funakoshi Co., Ltd. In any case, a recombinant vector can be obtained corresponding to the parent vector used.

A general procedure for preparing recombinant plasmids is described in J. Samblook et al., Molecular Cloning 2nd ed., Cold Spring Harbor Laboratory Press (1989) (hereinafter, this literature is referred to as "Molecular Cloning").

The transformant may be prepared by inserting the above recombinant plasmid into a host.

The host, which is not particularly limited as long as the Reg protein DNA in the recombinant plasmid is expressed, includes, for example, yeast such as *Saccharomyces cerevisiae, Pichia pastoris*, etc., *Escherichia* bacteria such as *Escherichia coli*, etc., *Bacillus* bacteria such as *Bacillus subtilis*, etc.

In inserting a recombinant plasmid into a host, for example, a host cell is converted into spheroplast or protoplast, into which a recombinant plasmid is inserted by means of electroporation, calcium chloride transformation or Tris-PEG method. These operations may be appropriately selected according to the sort of host.

A general procedure for preparing a transformant utilizing a recombinant plasmid is described in detail in a literature, "Molecular Cloning", and so on. For the purpose of preparing a transformant by utilizing a recombinant plasmid, a variety of kits have been commercially available. For example, a kit using yeast, *Pichia pastoris*, is commercially available from Funakoshi Co., Ltd. (catalogue no. IV-1750-01; manufacturer: Invitrogen Corp.), and a transformant can be prepared according to an instruction manual attached to the kit.

A specific example of transformants used in preparation of Reg proteins by using transformants includes a recombinant yeast, *Pichia pastoris* GS115 strain (Human REGIα-13) containing a vector into which human REGIα cDNA has been inserted. The GS115 strain (Human REGIα-13) was deposited at Agency of Industrial Science and Technology, National Institute of Bioscience and Human-Technology (Zip code 305-8566; 1-3, Higashi 1-chome, Tukuba city, Ibaragi, Japan) as the accession no. FERM P-17358 on Apr. 5, 1999, and transferred to the international deposition as FERM BP-7111 on Mar. 30, 2000 under the Budapest Treaty.

Incubation of a transformant is carried out by placing a transformant on a culture medium on which the transformant can be grown, and then shaking or standing at a suitable temperature.

As a culture medium, those containing carbon sources and nitrogen sources may be used. The carbon source includes, for example, sugar, alcohol, organic acid, and the like; the sugar is exemplified by glucose, starch, dextrose, molasses, etc., the alcohol by methanol, ethanol, glycerol, etc., and the organic acid by citric acid, malonic acid, etc. The nitrogen source includes, for example, organic nitrogen source, inorganic nitrogen source, etc.; the organic nitrogen source is exemplified by peptone, casein, polypeptone, bactotryptone, meat extract, yeast extract, casamino acid, glycine, etc.; the inorganic nitrogen source by ammonium sulfate, ammonium nitrate, etc.

When the transformant is auxotrophy, nutritional materials required for the growth are added to the medium. Such nutritional materials include, for example, amino acids, vitamins, nucleic acids, salts, and the like.

As for the medium, for example, a synthetic medium mainly composed of alcohols and organic nitrogen sources may be used.

When a solid medium is used as a medium, additionally agar is added.

In order to maintain the recombinant plasmid stably and inhibit growth of strains having no recombinant plasmid, an antibiotic or antibiotics may be added to the medium. Such antibiotics include, for example, penicillin, erythromycin, kanamycin, neomycin, chloramphenicol, bacitracin, D-cycloserine, ampicillin, and the like.

Moreover, if required, as a defoaming agent, soybean oil, lard oil, various surface-activating agents, etc., may be added.

The pH of the medium is usually kept in a range of 4–9, at which the transformant can grow. When yeast *Pichia pastoris* is used as a host, the medium is preferably kept at pH 5.0–7.0.

The incubation temperature is usually kept, for example, at 15–42° C., preferably at 24–37° C.

The incubation time is variable depending on the sort of host, physical state of the medium (solid or liquid), incubation apparatus, incubation temperature, etc. For example, when yeast *Pichia pastoris* is used as a host at an incubation temperature of 15–42° C., the incubation time is usually 12–96 hours, preferably 60–84 hours.

As described above, a transformant into which a gene coding for a Reg protein has been introduced is incubated to accumulate the Reg protein in a culture comprising the culture broth and the transformant after incubation; the culture is recovered, from which the objective Reg protein can be purified.

For example, when the Reg protein generated in a host is a fused protein composed of a signal sequence and an amino acid sequence of the Reg protein, the signal sequence is eliminated from the fused protein by signal peptidase of the transformant, and the Reg protein is secreted from the transformant. Thus, the supernatant is collected as a culture after incubation of the transformant, from which the Reg protein is purified preferably in a conventional manner.

Alternatively, the incubated transformant is collected as a culture, which is crushed or dissolved to give a crushed liquid or solution, from which the Reg protein is purified.

In addition, purification from the culture broth and from the incubated transformant as for a culture may be combined to improve yield of the objective Reg protein. Crushing of the transformant may be carried out, for example, by a method for physically crushing the transformant. For example, the transformant is suspended in a buffer, to which ultrasonic wave is irradiated, or the transformant blended with quartz sand is suspended in a buffer. On the other hand, dissolution of the transformant may be achieved, for example, by a method for dissolving the cell wall of the transformant with an enzyme and a surfactant. When the host transformant is *Escherichia coli*, lysozyme as enzyme and sodium dodecyl-sulfate (hereinafter abbreviated to SDS) as surfactant may be used.

In purifying the objective Reg protein from the resulting crushed liquid or dissolved solution, for example, the crushed liquid or dissolved solution is centrifuged to remove cell residue and to obtain a supernatant, the resulting supernatant is treated with addition of ammonium sulfite at a concentration at which no precipitate of Reg protein is generated. The mixture is stirred, centrifuged to remove the precipitate and to obtain a supernatant, to which is further added ammonium sulfate at a concentration at which precipitate of Reg protein is generated. The precipitate generated after stirring can be recovered by centrifugation. It is preferable to confirm the presence of Reg proteins in the supernatant and the precipitated fraction by sampling in the final centrifugation since the supernatant sometimes contains the objective Reg protein. In purifying the objective Reg protein from the supernatant of the culture after incubation of the transformant, for example, the culture broth is centrifuged to remove the cells as precipitate, and the supernatant is adjusted at pH 3.5 with addition of acetic acid and mounted on an ion-exchange column to absorb the Reg protein. After washing the column with a sodium acetate buffer, the adsorbed Reg protein is eluted with a sodium acetate buffer containing 1M NaCl to obtain the Reg protein.

An alternative method other than the above-mentioned methods for purifying the objective Reg protein from the crushed liquid, dissolved solution or supernatant after incubation of the transformant, includes fractionation by salting-out, ethanol precipitation, gel filtration, affinity chromatography, hydrophobic chromatography, and the like. These purification methods may be used alone or in a combination of two or more. The above methods for purification of proteins are described in detail in the literatures "Molecular Cloning" and "Basic Experimental Method for Proteins and Enzymes" (2nd revised edition, Buichi Kajio editor, Nankodo Co., Ltd. (1994)).

In specific examples of production of Reg proteins using a genetic recombination, the Reg proteins can also be produced according to the methods as described in Japanese Patent Application Laid-Open No. Hei 1-137994/1989 and Japanese Patent Application Laid-Open No. Hei 6-29963/1994.

In producing Reg proteins by means of chemical syntheses, a sequential 10 to 30 amino acid sequence as a part of the Reg protein amino acid sequence may be synthesized according to a known method for peptide syntheses. The peptide synthesis may be achieved, for example, by a solid phase method in which a peptide chain is extended from the C-terminal on a polymer carrier, or by a liquid phase method without using any carrier. In the above solid phase method, the peptide synthesis can be achieved by using a commercially available peptide synthesizer. Moreover, one or two or more of the peptide chains synthesized as described above may be linked each other to form a protein.

In producing the purified Reg proteins from organs, body fluid or secretion, the organs, body fluid or secretion used as raw materials, which is not particularly limited as long as they contain Reg proteins, include pancreas, Langerhans islet cells, exocrine pancreatic glands, nerve cells and various cancer cells including hepatoma, colon cancer, cancer of small intestine, etc.

As a method to obtain a crushed or dissolved solution from organs, the above-mentioned method for crushing or dissolving the transformant may be utilized.

As a method for purifying the Reg proteins form organs, body fluid or secretion, the same method as that described above for purification of the Reg proteins from the transformant may be utilized.

More specific examples of method for purifying Reg proteins include methods as described in Guy-Crotte et al., Biochemical and Biophysical Research Communications, Vol. 125, 516–523 (1984); De Caro A M et al., European Journal of Biochemistry, Vol. 168, 201–207 (1987); and De Caro AM et al., Biochimica et Biophysica Acta, Vol. 994, 281–284 (1989).

In the present invention, a method for detecting an anti-Reg protein autoantibody, which is not particularly limited as long as the method comprises the steps of bringing a specimen into contact with an antigen component capable of binding specifically to the anti-Reg protein autoantibody and detecting the formation of an immune complex resulting from the reaction of the anti-Reg protein autoantibody with the antigen component capable of binding specifically to the anti-Reg protein autoantibody, includes Western blotting technique, immunoassay utilizing various labels, latex agglutination test using latex carrier particles, and the like.

Immunoassay utilizing various labels includes, for example, radioimmunoassay (RIA), fluorescent immunoassay (FIA), luminescent immunoassay, enzyme-linked immunoadsorbent assay (ELISA), immunochromatography, and the like.

A method for detecting an anti-Reg protein autoantibody by means of Western blotting technique may be carried out, for example, by separating the above Reg proteins by electrophoresis, transcribing on a porous membrane, blocking the porous membrane (hereinafter referred to transcriptional membrane) to inhibit non-specific reaction with a specimen, bringing the transcriptional membrane into contact with a specimen for a certain period of time, by which operation an anti-Reg protein autoantibody in the specimen if any is bound to an antigen immobilized on the above-mentioned transcriptional membrane to form an immune complex, if required washing it, and then bringing it into contact with a labeled second antibody capable of binding to the anti-Reg protein autoantibody (in some cases, the specimen may be allowed to contact with the labeled second antibody at the same time).

If the above immune complex is formed, a labeled second antibody is bound thereto, by which the labeled second antibody is also fixed on the transcriptional membrane. Thereafter, the amount of the labeled second antibody binding to the transcriptional membrane is determined according to the measurement method depending on the label used, and the existence or amount of the anti-Reg protein autoantibody can be confirmed or obtained from the measured values.

The existence or amount of the anti-Reg protein autoantibody may be detemined, for example, by measuring a specimen containing no anti-Reg protein autoantibody and a specimen containing a prefixed amount of anti-Reg protein autoantibody simultaneously with measurement of a specimen to be tested, and comparing the values of respective specimens. Thus, titer of the anti-Reg protein autoantibody can be expressed as the values converted into the standard values.

In the present invention, "measurement" means not only quantitative or semi-quantitative detection but also qualitative detection.

Electrophoresis of Reg proteins may be achieved, for example, by a variety of known electrophoreses such as SDS polyacrylamide electrophoresis, native polyacrylamide gel electrophoresis, gel isoelectric focusing, etc. Among them, SDS polyacrylamide electrophoresis is preferred since the proteins can be separated based on their molecular weight and the transcription is efficient.

As a method of subsequent transcription of the protein molecule separated by electrophoresis onto a porous membrane, for example, a well-known method utilizing a capillary phenomenon (capillary method), a method utilizing natural diffusion ability (diffusion method) and a method utilizing electrophoresis (electrophoresis), and the like are included. Among them, electrophoresis is preferred in view of operation time as well as quantitative characteristic and reproducibility in detection.

As for a porous membrane, a well-known membrane used in Western blotting technique such as nitrocellulose membrane, polyvinylidene difluoride (PVDF) membrane, etc. may be utilized. Preferably, PVDF membrane is preferred in view of high binding capacity to proteins in transcription.

As for a blocking agent for transcriptional membranes, for example, a well-known solution used in Western blotting technique such as a solution of casein material including non-fat milk, a solution of gelatin material, a solution of bovine serum ablumin (BSA) material, etc., may be utilized.

A specimen may be allowed to react directly with a transcriptional membrane, and when the antibody titer is high, it may be diluted. When a diluted specimen is used, a well-known solution used in Western blotting technique such as a phosphate buffered saline (hereinafter abbreviated to PBS), phosphate buffer, etc., may be utilized, but it is preferred to use the same solution as that used in blocking in view of decreasing non-specific adsorption.

As the washing solution in washing used after the reaction with a specimen, a well-known solution used in western blotting technique may be utilized, including, for example, PBS, phosphate buffer, etc. In addition, a buffer solution containing a non-ionic surfactant such as Tween 20 at a concentration of 0.05–5% by weight may be used.

As the labeled second antibody which is used for detecting the formation of an immune complex resulting from the reaction of an anti-Reg protein autoantibody with an antigen component capable of binding specifically to the anti-Reg protein autoantibody, antibodies prepared by labeling an antibody against an autoantibody in a specimen with a variety of labeling materials are exemplified, though there is no limitation as long as they can bind as labeled second antibodies to the anti-Reg protein autoantibody on a transcriptional membrane. The antibody which can be labeled includes, for example, anti-IgG antibody, anti-IgM antibody, anti-IgA antibody, anti-IgE antibody, etc., or their partially decomposed fragments (F(ab')$_2$, Fab, etc.). The second antibodies specific to respective autoantibodies may be used alone or in combination. The second antibodies may be either polyclonal or monoclonal, but the polyclonal antibodies are preferred in view of sensitivity. Moreover, the antibody that has been purified by affinity purification with an antibody molecule as ligand is more preferred in view of sensitivity.

As for the labeling material used in labeling of the second antibodies, for example, an enzyme or radioactive isotope can be utilized. The enzyme includes, for example, maleate dehydrogenase (enzyme no. 1.1.1.37), glucose-6-phosphate dehydrogenase (enzyme no. 1.1.1.49), glucose oxidase (enzyme no. 1.1.3.4), horseradish peroxidase (enzyme no. 1.11.1.7), acetylcholine esterase (enzyme no. 3.1.1.7), alkaline phosphatase (enzyme no. 3.1.3.1), glucoamylase (enzyme no. 3.2.1.3), lysozyme (enzyme no. 3.2;1.17), β-galactosidase (enzyme no. 3.2.1.23), and the like. Among them, labeling with horseradish peroxidase is preferred since it can be used in a highly sensitive detection system in which light is emitted from luminol by adding hydrogen peroxide to a substrate to expose the x-ray film.

Alternatively, in place of an enzyme, RI may be attached to the second antibody to obtain a signal of RI activity. As the solution used in the reaction of the second antibody with the transcription membrane, a well-known solution used in Western blotting technique such as blocking solution, PBS, tris-buffer solution may be used. In the washing operation after the reaction of the second antibody, the aforementioned various washing solutions can be utilized.

In order to detect the anti-Reg protein autoantibody by immunoassay utilizing a variety of labeling materials, for example, the Reg protein is immobilized physically or chemically on a carrier to yield an immobilized antigen, which is allowed to contact with a specimen under warming for a certain period of time. Thus, if the anti-Reg protein autoantibody exists in the specimen, the autoantibody is bound to the immobilized antigen to form an immune complex on the carrier. This is, if required, washed, and then allowed to contact with a labeled second antibody against the above-mentioned antibody in the specimen (in some cases, the specimen may be allowed to contact with the labeled second antibody at the same time).

If the immune complex is formed, the labeled second antibody is bound thereto, which is thus immobilized on the carrier. Thereafter, the labeled second antibody bound on the carrier or the labeled second antibody free from the carrier is quantitatively analyzed according to a measurement method depending on its label. Thus, the existence or amount of the anti-Reg protein autoantibody can be confirmed from the measured values.

The carriers, which are not particularly limited as long as they are able to immobilize the antigen, include, for example, plastic materials such as polystyrene, vinyl chloride, etc., fiber materials such as cellulose, nitrocellulose, nylon, etc., inorganic materials such as glass, silica gel, etc., erythrocytes, liposome, PDVF, and the like. The shape of them may be in any form of microtiter plate, beads, magnetic beads, paper disc, membrane, string, and the like. For convenience, polystyrene beads or microtiter plate are preferably used, and a microtiter plate is more preferable.

In order to immobilize the Reg protein physically on a carrier, for example, a solution containing the Reg protein is allowed to contact with a carrier at a low temperature (e.g., 4° C.) overnight.

In order to immobilize the above-mentioned Reg protein chemically on a carrier, for example, the Reg protein is admixed with a carbodiimide and a carrier having carboxyl groups on the surface, and the mixture is allowed to stand.

In order to prevent non-specific binding of other antibodies and the like in a specimen on the carrier, it is appropriate to block the surface of the carrier with non-fat milk, bovine serum albumin (BSA), etc., prior to addition of the specimen.

As for a washing solution, for example, a tris-buffer or phosphate buffer containing a surfactant may be used.

In the labeled second antibody to be used, the antibody to be labeled may be the antibody exemplified in Western blotting technique.

As the labeling materials used in labeling of the second antibody, fluorescent materials such as fluorescein, metal colloids such as gold colloid, non-metal colloids such as selenium colloid, colored particles such as colored resin particles, colored liposome dye particles, and the like, may be used in addition to the labeling materials as exemplified in Western blotting technique.

Among these labeling materials, it is preferable to use an enzyme in view of sensitivity, safety and convenience, etc. As for the enzyme-labeled antibodies, alkaline phosphatase-labeled antibodies or horseradish peroxidase-labeled antibodies are preferably used in view of the point that easy and high sensitive measurement is possible. These enzyme-labeled antibodies are commercially available.

In order to link the antibody to the labeling material, a chemical material such as biotin, avidin, streptoavidin, digoxigenin, etc., may be made to intervene between the antibody and the labeling material.

In detecting the anti-Reg protein autoantibodies by utilizing a latex agglutination method, for example, an antigen component capable of binding specifically to the anti-Reg protein autoantibody is immobilized physically or chemically on latex particles (carrier) to prepare an immobilized antigen, which is then allowed to contact with a specimen under warming for a certain period of time, and turbidity of the mixture of the specimen and the immobilized antigen is measured. The contact of the immobilized antigen with the specimen, if an anti-Reg protein autoantibody exists in the specimen, could lead to formation of an immune complex by antigen-antibody reaction. During this reaction, since the antibody molecule has two sites binding to the antigen, it works as a crosslinking agent to generate agglutination reaction. This reaction increases turbidity of the mixture of the specimen and the immobilized antigen, and the turbidity is measured visually or with an absorptiometer.

In place of latex particles in the latex agglutination method, other various particles such as erythrocytes or liposome may be used.

In the reagents for diagnosing autoimmune diseases, diabetes mellitus, insulin-dependent diabetes mellitus, and non-insulin-dependent diabetes mellitus of the present invention, the composition of the reagent is variable depending on the method for detecting the anti-Reg protein autoantibody. However, as long as the reagent contains an antigen component capable of binding specifically to the anti-Reg protein autoantibody as a major effective component, there is no particular limitation in the composition of reagent for detecting the anti-Reg protein autoantibodies as mentioned above.

As for the antigen component capable of binding specifically to the anti-Reg protein autoantibody, the antigen components as exemplified in the above-mentioned method for detecting the anti-Reg protein autoantibodies may be used.

As for the composition of the diagnostic reagent of the present invention, for example, when Western blotting technique is used, a reagent comprising separately a Reg protein agent prepared for SDS polyacrylamide electrophoresis and a labeled second antibody which reacts with the anti-Reg protein autoantibody to be detected may be exemplified. In the diagnostic reagent for the anti-Reg protein autoantibodies utilizing an immunoassay using a variety of labeled materials, for example, a reagent comprising separately a carrier on which a Reg protein is immobilized and a labeled second antibody which reacts with the anti-Reg protein autoantibody to be detected may be exemplified. In the diagnostic reagents for the anti-Reg protein autoantibodies utilizing latex agglutination, for example, a reagent of latex particles (carrier) on which a Reg protein is immobilized may be exemplified.

As for the labeled second antibody used in the above diagnostic reagents, the labeled second antibody as exemplified in the above-mentioned method for detecting the anti-Reg protein autoantibodies may be used. As for the labeled second antibodies to be used in one specimen, it is preferable to use one or more of the labeled antibodies against any classes of antibodies. These labeled second antibodies may be provided separately or as a mixture.

In the diagnostic reagents of the present invention, in addition to the above composition of the reagent, other auxiliary agents or auxiliary materials may be used in combination to diagnostic kits.

For example, in the above diagnostic reagents utilizing Western blotting technique, the other component includes, for example, gel for electrophoresis, membrane for transcription, blocking solution, negative control specimen, positive control specimen, washing solution, reaction substrate where the labeling material is an enzyme and the like, diluent, sensitizer, reaction-terminating agent, and the like. These may be used alone or in combination. The form of the reagent may be, for example, a kit enveloping necessary amounts of the above components. In the diagnostic reagents using an immunoassay with the above various labeling materials, the other component includes, for example, negative control specimen, positive control specimen, washing solution, reaction substrate where the labeling material is an enzyme and the like, diluent, sensitizer, reaction-terminating agent, and the like. These may be used alone or in combination. The form of the reagent may be, for example, a kit enveloping necessary amounts of the above components, or bulk of a single product of these reagents.

In the diagnostic reagents using the above latex agglutination, the other component includes, for example, negative control specimen, positive control specimen, sensitizer, and the like. The sensitizer includes, for example, bovine serum albumin, polyethylene glycol, and the like.

In the diagnostic reagents of the present invention, the objective diseases to be diagnosed or predicted, which is not particularly limited as long as the diseases are autoimmune diseases caused by the existence of the anti-Reg protein autoantibodies, include, for example, diabetes mellitus, insulin-dependent diabetes mellitus, non-insulin-dependent diabetes mellitus, hepatoma, colon cancer, cancer of small intestine, pancreatitis, gastric ulcer, and Alzheimer's disease. Among them, diabetes mellitus is preferred in view of high positive rate, and more preferred are insulin-dependent diabetes mellitus and non-insulin-dependent diabetes mellitus.

BEST MODE FOR CARRYING OUT THE INVENTION

The present invention will be explained in more detail by the following Examples.

EXAMPLE 1

Measurement of Sera of IDDM Patients and Healthy Volunteers by Western Blotting Technique (1) Specimen As specimens, sera collected from 75 healthy volunteers (Non-DM) and 202 IDDM patients were used.

(2) Method for Producing Reg Protein

Human REG Iα cDNA in full length was inserted into pPIC 3.5 vector (purchased from Funakoshi Co., Ltd.; manufactured by Invitrogen Corp.). The resulting expression vector was transformed into yeast *Pichia pastoria* GS115 (purchased from Funakoshi Co., Ltd.; manufactured by Invitrogen Corp.) to yield recombinant yeast producing and secreting human Reg protein at culture medium.

This recombinant yeast *Pichia pastoria* GS115 (Human REG Iα-13) containing a vector into which was inserted the above human REG Iα cDNA was deposited at Agency of Industrial Science and Technology, National Institute of Bioscience and Human-Technology (Zip code 305-8566; 1-3, Higashi 1-chome, Tukuba city, Ibaragi, Japan) as the accession no. FERM P-17358 on Apr. 5, 1999, and transferred to the international deposition as FERM BP-7111 on Mar. 30, 2000 under the Budapest Treaty.

This recombinant yeast was incubated in a culture broth of BMGY medium (yeast extract 1%, peptone 2%, 100 mM potassium phosphate buffer (pH 6.0), yeast nitrogen base without amino acids 1.34%, biotin $4 \times 10^{-5}$%, glycerol 1%) at 30° C. for 18 hours. The cultured broth was subjected to a centrifuge, the resulting cells obtained as precipitate was suspended into a culture broth of BMMY medium (yeast extract 1%, peptone 2%, 100 mM potassium phosphate buffer (pH 6.0), yeast nitrogen base without amino acids (YNB) 1.34%, biotin $4 \times 10^{-5}$%, methanol 1%) and incubated at 30° C. for 72 hours. During incubation, methanol was added in an amount corresponding to 0.5% of the culture broth every 24 hours.

After completion of the incubation, the culture broth was subjected to centrifugal separation to remove cells as precipitate. The supernatant was adjusted at pH 3.5 with addition of acetic acid, and Reg proteins were adsorbed on an ion-exchange column by using an ion-exchange column chromatography apparatus STREAMLINE SP (Pharmacia Biotec Co., Ltd.). The column was washed with 50 mM sodium acetate (pH 3.5) and then eluted with 50 mM sodium acetate (pH 3.5) containing 1M Nacl to yield Reg protein.

(3) Detection of Anti-Reg Protein Autoantibody by Western Blotting Technique

Reg protein (20 μg) was treated with SDS in a well-known method, then subjected to electrophoresis on 15% SDS polyacrylamide gel (9×6 cm), and when electrically transcribed on a hydrophobic PVDF membrane (Japan Millipore Co., Ltd.). This transcribed membrane was blocked in 5% non-fat milk solution.

The serum as specimen was then diluted 1000–20000 times with 5% non-fat milk solution, and incubated with the blocked transcription membrane using a Screener Blotter Mini 56. After gentle washing, the transcription membrane was allowed to react with a horseradish peroxidase-lebeled rabbit anti-human antibody (Manufactured by American Qualex International, Inc.; marketed by Cosmo Bio Co., Ltd.) diluted 1000–20000 times. Luminous reaction was carried out with Col a detection kit, ECL Western Blotting Detection System (Amersham Co., Ltd.) using chemiluminescence for Western blotting technique and exposed to an X-ray film. After developing the film, the film was dried, and scanned with a scanner to take the data in a computer as an image data.

Figure 1:
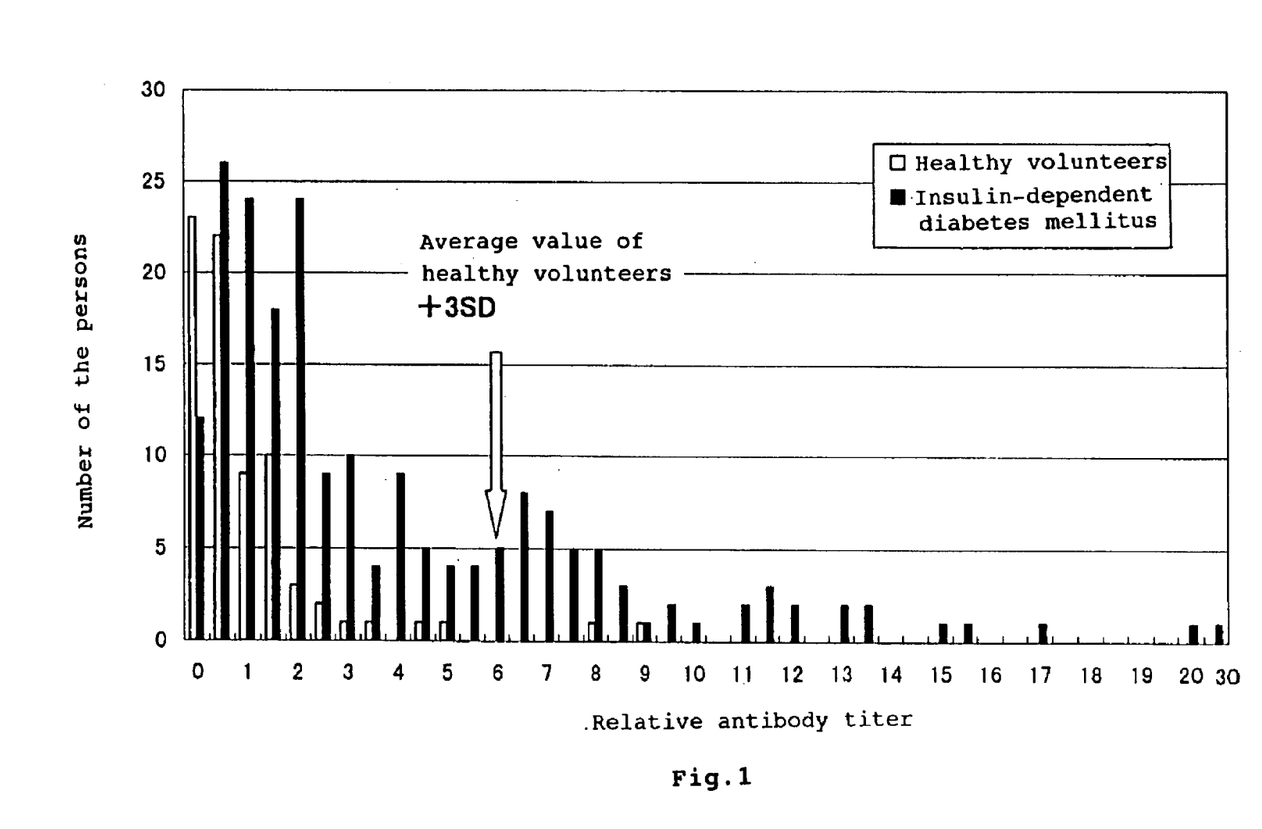
FIG. 1 is a graph showing distribution of the relative antibody titers of anti-Reg protein autoantibodies in the patients of insulin-dependent diabetes mellitus and in the healthy volunteers.

Anti-Reg protein autoantibody was linked to Reg protein to form an immune complex, to which was bound the labeled second antibody. Therefore, the substrate emitted light, by which was exposed an X-ray film to give bands. The reflection absorbance of resulting bands was measured by an NIH image software (attached to "Very easy practice! Image Analysis Text"—NIH Imgage New Course, Kojima et al., edition, Yodo-sha (1997)). Absorbance of one specimen of healthy volunteers, which was nearest to the average value, was assumed to be 1, and the measured absorbance was expressed as a relative antibody titer of the anti-Reg protein autoantibodies. Table 1 and FIG. 1 show distribution of the relative antibody titers of anti-Reg protein autoantibodies in the patients of insulin-dependent diabetes mellitus and in the healthy volunteers. The average value of relative antibody titers in the healthy volunteers was 1.34, and the standard deviation (SD) was 1.59. Thus, the patients whose relative antibody titer was more than 3SD against the average value of the relative antibody titer of the healthy volunteers, i.e., 6.12 or more of the relative antibody titer were identifying to be positive of anti-Reg protein autoantibodies. Table 2 shows the number of positive and negative persons in the patients of insulin-dependent diabetes mellitus and in the healthy volunteers as well as the positive rate. The number of persons positive to anti-Reg protein autoantibodies was 49 in a group of diabetes mellitus, and the positive rate was 24%. On the other hand, the number of antibody-positive persons in the healthy volunteers was only 2, and the positive rate was 3% or less.

TABLE 1

Distribution of the relative antibody titers of anti-Reg protein autoantibodies

| Relative antibody titer | Patients of insulin-dependent diabetes mellitus (Number) | Healthy volunteer (Number) |
| --- | --- | --- |
| 0.0–0.5 | 12 | 23 |
| 0.5–1.0 | 26 | 22 |
| 1.0–1.5 | 24 | 9 |
| 1.5–2.0 | 18 | 10 |
| 2.0–2.5 | 24 | 3 |
| 2.5–3.0 | 9 | 2 |
| 3.0–3.5 | 10 | 1 |
| 3.5–4.0 | 4 | 1 |
| 4.0–4.5 | 9 | 0 |
| 4.5–5.0 | 5 | 1 |
| 5.0–5.5 | 4 | 1 |
| 5.5–6.0 | 4 | 0 |
| 6.0–6.5 | 5 | 0 |
| 6.5–7.0 | 8 | 0 |
| 7.0–7.5 | 7 | 0 |
| 7.5–8.0 | 5 | 0 |
| 8.0–8.5 | 5 | 1 |
| 8.5–9.0 | 3 | 0 |
| 9.0–9.5 | 1 | 1 |
| 9.5–10.0 | 2 | 0 |
| 10.0–10.5 | 1 | 0 |
| 10.5–11.0 | 0 | 0 |
| 11.0–11.5 | 2 | 0 |
| 11.5–12.0 | 3 | 0 |
| 12.0–12.5 | 2 | 0 |
| 12.5–13.0 | 0 | 0 |
| 13.0–13.5 | 2 | 0 |
| 13.5–14.0 | 2 | 0 |
| 14.0–14.5 | 0 | 0 |
| 14.5–15.0 | 0 | 0 |
| 15.0–15.5 | 1 | 0 |
| 15.5–16.0 | 1 | 0 |
| 16.0–16.5 | 0 | 0 |
| 16.5–17.0 | 0 | 0 |
| 17.0–17.5 | 1 | 0 |
| 17.5–18.0 | 0 | 0 |
| 18.0–18.5 | 0 | 0 |
| 18.5–19.0 | 0 | 0 |
| 19.0–19.5 | 0 | 0 |
| 19.5–20.0 | 0 | 0 |
| 20.0–25.0 | 1 | 0 |
| 25.0–30.0 | 1 | 0 |
| Total (Number) | 202 | 75 |

TABLE 2

| | Positive Rate | |
| --- | --- | --- |
| | Patients of insulin-dependent diabetes mellitus | Healthy volunteers |
| Positive persons (number) | 49 | 2 |
| Negative persons (number) | 153 | 73 |
| Positive rate (%) | 24.3 | 2.67 |

EXAMPLE 2

Measurement of Sera of NIDDM Patients by Western Blotting Technique (1) Specimen As specimens, sera collected from 75 healthy volunteers (Non-DM) and 368 NIDDM patients were used.

(2) Detection of Anti-Reg Protein Autoantibodies by Western Blotting Technique

Figure 2:
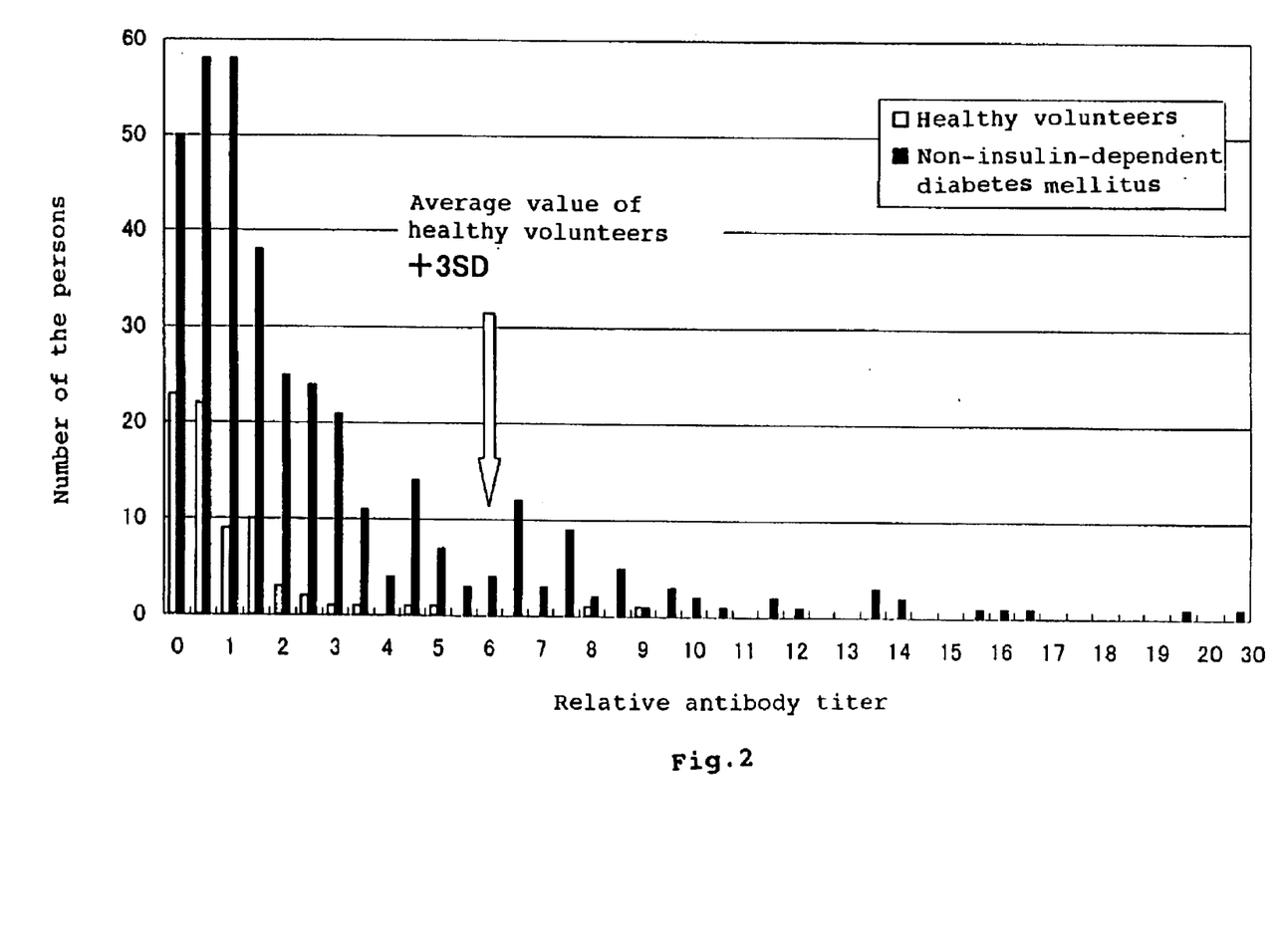
FIG. 2 is a graph showing distribution of the relative antibody titers of anti-Reg protein autoantibodies in the patients of non-insulin-dependent diabetes mellitus and in the healthy volunteers.

In the same manner as in Example 1, the anti-Reg protein autoantibody was detected by means of Western blotting technique. The reflection absorbance of bands given by exposure of an X-ray film was measured by an NIH image software in the same manner as in Example 1. Absorbance of one specimen of healthy volunteers used in Example 1, which was nearest to the average value, was assumed to be 1, and the measured absorbance was expressed as a relative antibody titer of the anti-Reg protein autoantobodies. Table 3 and FIG. 2 show distribution of the relative antibody titers of anti-Reg protein autoantibodies in the patients of non-insulin-dependent diabetes mellitus and in the healthy volunteers. In the same way as in Example 1, the patients whose relative antibody titer was more than 3SD against the average value of the relative antibody titer of the healthy volunteers, i.e., 6.12 or more of the relative antibody titer were identifying to be positive of anti-Reg protein autoantibodies. Table 4 shows the number of positive and negative persons in the patients of non-insulin-dependent diabetes mellitus and healthy volunteers as well as the positive rate. While the number of antibody-positive persons in the healthy volunteers was only 2, and the positive rate was 3% or less, the number of persons who were recognized positive to anti-Reg protein autoantibodies was 55, i.e., 15%, in non-insulin-dependent diabetes mellitus.

From the above results, it was found that 24% or more of the patients of insulin-dependent diabetes mellitus and 15% or more of the patients of non-insulin-dependent diabetes mellitus were due to autoimmune diabetes mellitus caused by the existence of anti-Reg protein autoantibodies. The above cause was so far unknown. From the results shown in Table 2, it is presumed that in two healthy volunteers from whom the anti-Reg protein autoantibody was detected, autoimmune diabetes mellitus or insulin-dependent diabetes mellitus or non-insulin-dependent diabetes mellitus might be developed in the future. Detection of the anti-Reg protein autoantibodies according to the present invention permits diagnosis of diseases of so far unknown cause being autoimmune diabetes mellitus or insulin-dependent diabetes mellitus or non-insulin-dependent diabetes mellitus, or permits prediction of future possibility of them.

TABLE 3

Distribution of the relative antibody titers of anti-Reg protein autoantibodies

| Relative antibody titer | Patients of non-insulin-dependent diabetes mellitus (Number) | Healthy volunteer (Number) |
| --- | --- | --- |
| 0.0–0.5 | 50 | 23 |
| 0.5–1.0 | 58 | 22 |
| 1.0–1.5 | 58 | 9 |
| 1.5–2.0 | 38 | 10 |
| 2.0–2.5 | 25 | 3 |
| 2.5–3.0 | 24 | 2 |
| 3.0–3.5 | 21 | 1 |
| 3.5–4.0 | 11 | 1 |
| 4.0–4.5 | 4 | 0 |
| 4.5–5.0 | 14 | 1 |
| 5.0–5.5 | 7 | 1 |
| 5.5–6.0 | 3 | 0 |
| 6.0–6.5 | 4 | 0 |
| 6.5–7.0 | 12 | 0 |
| 7.0–7.5 | 3 | 0 |
| 7.5–8.0 | 9 | 0 |
| 8.0–8.5 | 2 | 1 |
| 8.5–9.0 | 5 | 0 |
| 9.0–9.5 | 1 | 1 |
| 9.5–10.0 | 3 | 0 |
| 10.0–10.5 | 2 | 0 |
| 10.5–11.0 | 1 | 0 |
| 11.0–11.5 | 0 | 0 |
| 11.5–12.0 | 2 | 0 |
| 12.0–12.5 | 1 | 0 |
| 12.5–13.0 | 0 | 0 |
| 13.0–13.5 | 0 | 0 |
| 13.5–14.0 | 3 | 0 |
| 14.0–14.5 | 2 | 0 |
| 14.5–15.0 | 0 | 0 |
| 15.0–15.5 | 0 | 0 |
| 15.5–16.0 | 1 | 0 |
| 16.0–16.5 | 1 | 0 |
| 16.5–17.0 | 1 | 0 |
| 17.0–17.5 | 0 | 0 |
| 17.5–18.0 | 0 | 0 |
| 18.0–18.5 | 0 | 0 |
| 18.5–19.0 | 0 | 0 |
| 19.0–19.5 | 0 | 0 |
| 19.5–20.0 | 1 | 0 |
| 20.0–25.0 | 0 | 0 |
| 25.0–30.0 | 1 | 0 |
| Total (Number) | 368 | 75 |

TABLE 4

Positive Rate

| | Patients of non-insulin-dependent diabetes mellitus | Healthy volunteer |
| --- | --- | --- |
| Positive persons (number) | 55 | 2 |
| Negative persons (number) | 313 | 73 |
| Positive rate (%) | 14.95 | 2.67 |

INDUSTRIAL APPLICABILITY

According to a method for identifying autoimmune diseases of the present invention, it is possible to diagnose autoimmune diseases of so far unknown cause which diseases are caused by the existence of anti-Reg protein autoantibodies.

According to a method for identifying diabetes mellitus of the present invention, it is possible to diagnose diabetes mellitus of so far unknown cause which disease is caused by the existence of anti-Reg protein autoantibodies.

According to a method for identifying insulin-dependent diabetes mellitus of the present invention, it is possible to diagnose insulin-dependent diabetes mellitus of so far unknown cause which disease is caused by the existence of anti-Reg protein autoantibodies.

According to a method for identifying non-insulin-dependent diabetes mellitus of the present invention, it is possible to diagnose non-insulin-dependent diabetes mellitus of so far unknown cause which disease is caused by the existence of anti-Reg protein autoantibodies.

According to a method for detecting anti-Reg protein antibodies, it is possible to provide a method for detection that can be used for diagnosing autoimmune diseases, diabetes mellitus, insulin-dependent diabetes mellitus and non-insulin-dependent diabetes mellitus of so far unknown cause which diseases are caused by the existence of anti-Reg protein autoantibodies.

The reagent for diagnosing autoimmune diseases of the present invention permits diagnosis of autoimmune diseases of so far unknown cause which diseases are caused by the existence of anti-Reg protein autoantibodies.

The reagent for diagnosing diabetes mellitus as described in the present invention permits diagnosis of diabetes mellitus of so far unknown cause which disease is caused by the existence of anti-Reg protein autoantibodies.

The reagent for diagnosing insulin-dependent diabetes mellitus of the present invention permits diagnosis of insulin-dependent diabetes mellitus of so far unknown cause which disease is caused by the existence of anti-Reg protein autoantibodies.

The reagent for diagnosing non-insulin-dependent diabetes mellitus of the present invention permits diagnosis of non-insulin-dependent diabetes mellitus of so far unknown cause which disease is caused by the existence of anti-Reg protein autoantibodies.

What is claimed is:

1. A method for identifying a human autoimmune disease in a human patient suspected of having autoimmune disease, which comprises:

providing a specimen from the patient;

detecting a human anti-Reg protein autoantibody in the specimen; and identifying a human autoimmune disease in the patient by comparing a level of the human anti-Reg protein autoantibody in the specimen to an average level of human anti-Reg protein autoantibody in a healthy population which does not have a human autoimmune disease.

2. The method of claim 1, wherein the level of the human anti-Reg protein autoantibody in the specimen is indicative of autoimmune disease in the patient when the level in the sample is at least about 3 standard deviation units above the average level in the healthy population.

3. A method for identifying diabetes mellitus in a human patient suspected of having diabetes mellitus, which comprises:

providing a specimen from the patient;

detecting a human anti-Reg protein autoantibody in the specimen; and identifying diabetes mellitus in the patient by comparing a level of the human anti-Reg protein autoantibody in the specimen to an average level of human anti-Reg protein autoantibody in a healthy population which does not have diabetes mellitus.

4. The method of claim 3, wherein the level of the human anti-Reg protein autoantibody in the specimen is indicative of diabetes mellitus in the patient when the level in the sample is at least about 3 standard deviation units above the average level in the healthy population.

5. The method for identifying diabetes mellitus according to claim 3, wherein the diabetes mellitus to be identified is insulin-dependent diabetes mellitus or non-insulin dependent diabetes mellitus.

6. A method for detecting a human anti-Reg protein autoantibody which comprises:

providing a specimen;

bringing the specimen into contact with a human Reg protein capable of binding specifically to the human anti-Reg protein autoantibody in the specimen; and detecting an immune complex resulting from a reaction of the human anti-Reg protein autoantibody in the specimen with the human Reg protein capable of binding specifically to the human anti-Reg protein autoantibody in the specimen.

7. The method for detecting a human anti-Reg protein autoantibody according to claim 6, wherein the human Reg protein is an artificially synthesized Reg protein.

8. A reagent comprising latex particles, wherein a human Reg protein capable of binding specifically to a human anti-Reg protein autoantibody is directly immobilized to the latex particle.

9. The reagent according to claim 8, wherein the human Reg protein is an artificially synthesized Reg protein.

10. A reagent which comprises a human Reg protein capable of binding specifically to a human anti-Reg protein autoantibody and a labeled second antibody which reacts with the human anti-Reg protein autoantibody.

11. The reagent according to claim 10, wherein the human Reg protein is an artificially synthesized Reg protein.

* * * * *

UNITED STATES PATENT AND TRADEMARK OFFICE
CERTIFICATE OF CORRECTION

PATENT NO.    : 6,919,210 B1
DATED         : July 19, 2005
INVENTOR(S)   : Okamoto, Hiroshi

It is certified that error appears in the above-identified patent and that said Letters Patent is hereby corrected as shown below:

Title page,
Item [56], References Cited, OTHER PUBLICATIONS,
"Y. Yonemura" reference, "Sui Ra Tou Saisai to reg Idenshi" should read -- Sui Ra Tou Saisei to reg Idenshi --.

Column 19,
Lines 8-9, "non-insulin dependent" should read -- non-insulin-dependent --.
Line 11, "autoantibody which comprises:" should read -- autoantibody, which comprises: --

Signed and Sealed this

Twenty-fourth Day of January, 2006

JON W. DUDAS
*Director of the United States Patent and Trademark Office*